(12) United States Patent
Hewson et al.

(10) Patent No.: US 11,324,893 B2
(45) Date of Patent: May 10, 2022

(54) DOSE LIMITING MECHANISM

(71) Applicant: NORTON HEALTHCARE LIMITED, West Yorkshire (GB)

(72) Inventors: Karl James Hewson, Cambridgeshire (GB); George Bostock, Cambridgeshire (GB); George Robert Michael Savell, Cambridgeshire (GB)

(73) Assignee: Norton Healthcare Limited, West Yorkshire (GB)

( * ) Notice: Subject to any disclaimer, the term of this patent is extended or adjusted under 35 U.S.C. 154(b) by 97 days.

(21) Appl. No.: 16/332,198

(22) PCT Filed: Sep. 11, 2017

(86) PCT No.: PCT/EP2017/072723
§ 371 (c)(1),
(2) Date: Mar. 11, 2019

(87) PCT Pub. No.: WO2018/046721
PCT Pub. Date: Mar. 15, 2018

(65) Prior Publication Data
US 2019/0366007 A1 Dec. 5, 2019

(30) Foreign Application Priority Data

Sep. 12, 2016 (GB) .................................. 1615455

(51) Int. Cl.
*A61M 5/315* (2006.01)
*A61M 5/20* (2006.01)
*A61M 5/31* (2006.01)

(52) U.S. Cl.
CPC ...... *A61M 5/31536* (2013.01); *A61M 5/2033* (2013.01); *A61M 5/31541* (2013.01);
(Continued)

(58) Field of Classification Search
CPC ............ A61M 5/31536; A61M 5/2033; A61M 5/31541; A61M 5/31593;
(Continued)

(56) References Cited

U.S. PATENT DOCUMENTS

2003/0160072 A1* 8/2003 Geiser ............... A61M 5/31551
222/327
2006/0153693 A1 7/2006 Fiechter et al.
(Continued)

FOREIGN PATENT DOCUMENTS

FR 2531879 A1 2/1984
WO 01/19434 3/2001
(Continued)

OTHER PUBLICATIONS

International Search Report and Written Opinion PCT/EP2017/072723 dated Dec. 14, 2018, 17 pages.

*Primary Examiner* — Amber R Stiles
*Assistant Examiner* — Avery Smale
(74) *Attorney, Agent, or Firm* — BakerHostetler

(57) ABSTRACT

An injection device comprises a dose selector, rotatable by a user to set a dose to be ejected from the injection device and a drive assembly including a drive shaft (140) and a plunger element (145), the drive assembly being capable of providing an axial force for ejecting a dose of medicament from a medicament container. A dose limit nut (141) is provided which is rotationally coupled to but not axially coupled to said drive shaft. The plunger element is threaded so that the dose limit nut is engaged with said plunger element via said thread, in order to guide relative axial movement between the dose limit nut and the plunger element. The dose limit nut is provided with dose limiting endstops which are capable of limiting axial travel of said dose limit nut with respect to said plunger element, so as to limit maximum and minimum doses of medicament which
(Continued)

can be set by the user. In addition, the dose limit nut comprises a last dose rotary endstop feature which prevents further rotation of said dose limit nut with respect to said drive shaft so as to prevent the user setting a dose that is greater than an injectable volume of medicament remaining in said medicament container.

18 Claims, 19 Drawing Sheets

(52) U.S. Cl.
CPC .... *A61M 5/31551* (2013.01); *A61M 5/31593* (2013.01); *A61M 2005/3126* (2013.01); *A61M 2005/3154* (2013.01); *A61M 2205/582* (2013.01)

(58) Field of Classification Search
CPC ...... A61M 2005/3154; A61M 5/31583; A61M 5/31551; A61M 2005/3126; A61M 5/31511; A61M 5/31553; A61M 5/24; A61M 5/31535; A61M 5/20; A61M 5/31501; A61M 5/31528; A61M 5/31548; A61M 5/3155
See application file for complete search history.

(56) References Cited

U.S. PATENT DOCUMENTS

| | | | |
|---|---|---|---|
| 2012/0310206 A1* | 12/2012 | Kouyoumjian | A61M 5/31543 604/506 |
| 2015/0065963 A1* | 3/2015 | Kjeldsen | A61M 5/31535 604/207 |

FOREIGN PATENT DOCUMENTS

| | | | | |
|---|---|---|---|---|
| WO | 2006/086983 A1 | 8/2006 | | |
| WO | 2007/017052 A1 | 2/2007 | | |
| WO | WO-2008101829 A1 * | 8/2008 | ........ | A61M 5/31565 |
| WO | 2011/068531 A1 | 6/2011 | | |
| WO | 2013/178372 A1 | 12/2013 | | |
| WO | 2014/166886 A1 | 10/2014 | | |
| WO | 2014/166909 A1 | 10/2014 | | |
| WO | WO-2014166886 A1 * | 10/2014 | .............. | A61M 5/20 |
| WO | 2015/007820 A1 | 1/2015 | | |
| WO | 2015/007821 A1 | 1/2015 | | |
| WO | 2015/036345 A1 | 3/2015 | | |
| WO | 2015/181141 A1 | 12/2015 | | |
| WO | 2016/001298 A1 | 1/2016 | | |
| WO | 2016/055438 A1 | 4/2016 | | |

* cited by examiner

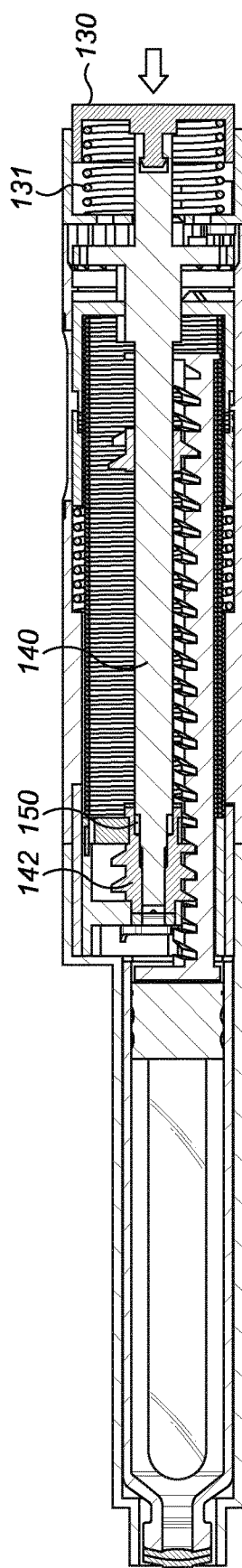
FIG. 11
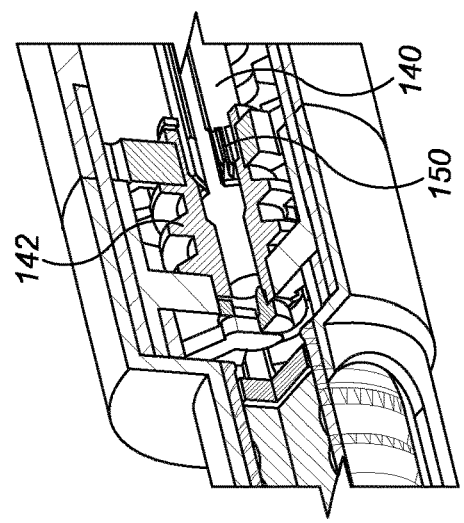
FIG. 11C
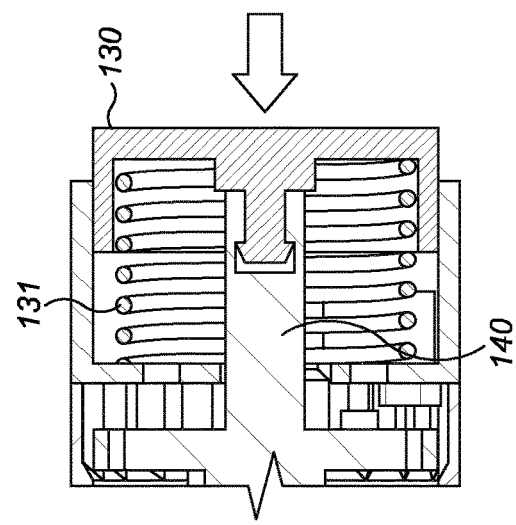
FIG. 11B
FIG. 11A

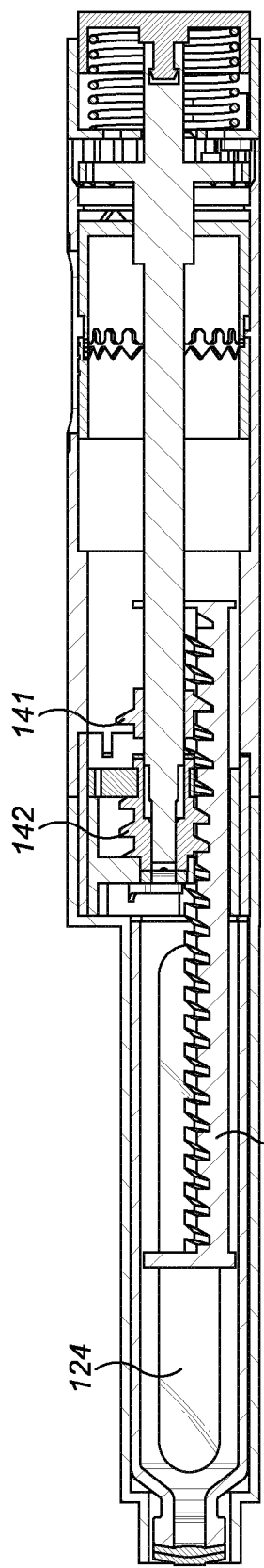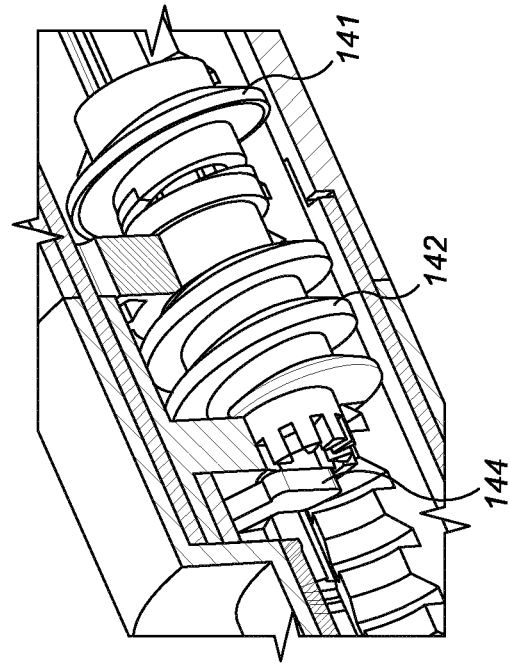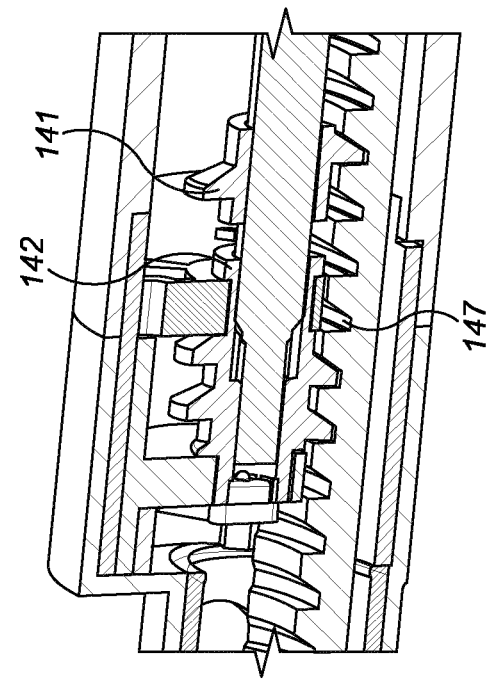
FIG. 14
FIG. 14B
FIG. 14A

DOSE LIMITING MECHANISM

CROSS-REFERENCE TO RELATED APPLICATIONS

This application is the National Stage of International Patent Application No. PCT/EP2017/072723, filed Sep. 11, 2017, which claims priority from Great Britain Patent Application No. 1615455.1 filed Sep. 12, 2016, the entire contents of both of which applications are incorporated herein by reference.

This disclosure relates to the field of a dose limiting mechanism for an injection device, preferably a reusable pen-injector injection device able to inject a selected dose of medicament.

BACKGROUND

Certain injection devices have a dose setting member, or dose selector, via which the user can select a desired dose of medicament to be delivered from a container of medicament associated with the injection device. The dose selector can commonly be actuated in one direction to increase the set dose ("dialing up") and actuated in another direction to decrease the set dose ("dialing down"). As the dose is dialed up or down, this correspondingly increases or decreases stored energy in the device (e.g. in a torsion spring).

During dose setting, it is desirable to be able to prevent a user from being able to dial up a dose that is larger than the quantity of medicament remaining in the container. This feature may be referred to as "last dose protection" or "last dose control".

Examples of injection devices with last dose protection features are described in WO2011/068531 (Becton Dickinson), WO01/19434 (Novo Nordisk) and WO2006/086983 (Novo Nordisk).

BRIEF SUMMARY OF THE DISCLOSURE

In accordance with an aspect of the present invention there is provided an injection device comprising:
  a. a dose selector, rotatable by a user to set a dose to be ejected from the injection device,
  b. a drive assembly including a drive shaft and a plunger element configured to move a stopper so as to expel medicament through an opening in a medicament container, the drive assembly being capable of providing an axial force for ejecting a dose of medicament from the medicament container,
  c. a dose limit nut rotationally coupled to but not axially coupled to said drive shaft,
wherein said plunger element is threaded so that the dose limit nut is engaged with said plunger element via said thread, in order to guide relative axial movement between the dose limit nut and the plunger element.
wherein said dose limit nut is provided with dose limiting endstop features which are capable of limiting axial travel of said dose limit nut with respect to said plunger element, so as to limit maximum and minimum doses of medicament which can be set by the user, and
wherein said dose limit nut further comprises a last dose rotary endstop feature which prevents further rotation of said dose limit nut with respect to said drive shaft so as to prevent the user setting a dose that is greater than an injectable volume of medicament remaining in said medicament container.

The dose limit nut conveniently provides both last dose protection and maximum/minimum dose limiting with a single component, reducing the total number of component parts required and simplifying the injection device's design.

In certain embodiments, one of said dose limiting endstop features also comprises said last dose rotary endstop feature. The dose limiting endstop features may be engageable with one or more formations in said thread of the plunger element. The or each formation in said thread may comprise a change in a depth of said thread.

In certain embodiments, said drive shaft is arranged concentrically around a first longitudinal axis with said medicament container and at least part of said drive assembly are arranged around a second longitudinal axis which is substantially parallel to but offset from the first longitudinal axis.

Preferably, the drive assembly comprises a rotational to axial coupling, where the drive assembly is rotationally drivable by a torsion spring and is arranged to provide said axial force for ejecting the dose from the medicament container.

In certain embodiments, said plunger element comprises a rack and the drive assembly further comprises a worm gear engaged in said rack, wherein rotation of said worm gear causes the rack to advance axially forward or backward with respect to said worm gear. Preferably, said last dose rotary endstop feature is engageable with said worm gear. The worm gear may be arranged around said first longitudinal axis and said rack may be arranged around said second longitudinal axis. The drive assembly may further comprise a worm gear rotational lock engageable with the worm gear, preferably engageable in a forward end thereof, so as to substantially prevent rotation of the worm gear. The worm gear rotational lock may be disengageable from the forward end of the worm gear by being pushed axially forward by the drive shaft. The drive assembly may further comprise means engageable between the drive shaft and the worm gear and which, when engaged, rotationally lock the drive shaft and worm gear together.

In certain embodiments, said dose limit nut has a male thread and said plunger element has a female thread. Alternatively, said dose limit nut has a female thread and said plunger element has a male thread.

Preferably said maximum dose is 100 IU and/or said minimum dose is 0 IU.

The injection device may further comprise a medicament container. Medicament may be contained in the medicament container. In certain embodiments, the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIGS. 11,11A-11C, 12 and 12A-12B illustrate dose delivery;

FIGS. 14 and 14A-14E illustrate last dose protection;

DETAILED DESCRIPTION

Figure 1:
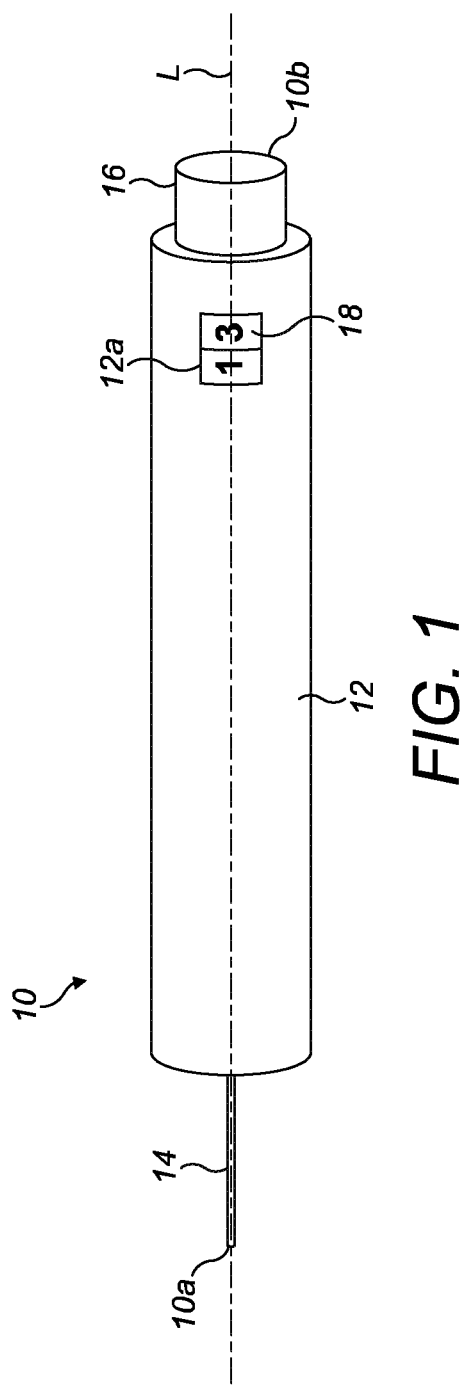
FIG. 1 shows an injection device in accordance with an embodiment of the present invention.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components.

The term "a rotational coupling" may refer to a coupling which enables a rotational force to be transmitted between the components.

The term "operatively connectable" may refer to at least two individual components which are releasably connectable together in such a way that the individual components can work together, for example wherein rotation of one of the individual components effects rotation of all of the operatively connected components.

The term "dose selector" may refer to a component or components which, when actuated by a user, enable a dose of medicament to be selected.

The term "dose indicator" may refer to a component or components which provide a display or indication to the user of the selected dose of medicament.

The term "splines" may refer to one or more ridges, ribs or other protrusions on one component which engage in corresponding grooves or the like on a second component to connect the two components together.

The term "a splined connection" may refer to a connection effected by one or more splines.

The term "forward" or "forwards" may refer to a direction towards the end of the injection device from which medicament is expelled.

The term "backward", "backwards", "rearwards" or "rearwardly" may refer to a direction away from the end of the injection device from which medicament is expelled.

The term "drive assembly" may refer to an assembly of components capable of using a driving force from, for example, a spring, to eject medicament from an injection device.

The term "backlash" may refer to a clearance caused by a gap between mechanical components.

The term "medicament" may include a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament" may refer to the medicament being contained within a suitable medicament container, such as a pre-filled syringe or cartridge, within the injection device.

The term "a force path" may refer to a path between two or more coupled components via which a force can be transmitted between the components. A force path may be "interrupted" if there is a gap between the two or more components, i.e. if they are no longer coupled. Transmission of force between coupled components may be "held back"

for example by a ratchet arrangement, but in such a case the force path is not "interrupted".

The term "a clutch" may refer to a component or feature suitable for operatively connecting two component parts either by a positive fit e.g. with teeth, splines, grooves or the like suitable for engaging and disengaging each other, or by a non-positive (e.g. frictional) connection or a combination thereof. Disengaging the clutch may interrupt a force path between two or more coupled components.

Description of First Example Embodiment

An injection device 10 according to an embodiment of the present invention is shown in FIG. 1. The injection device 10 is configured to deliver a dose of medicament and extends along a longitudinal axis L between a front end 10a and a rear end 10b of the injection device 10. The injection device 10 has a housing 12 and a needle 14 projecting from the housing 12 at the front end 10a. A dose selector 16 is provided at the rear end 10b and is arranged to permit the selection of a desired dose of medicament for delivery through the needle 12 into an injection site. The dose selector 16 is capable of being rotated about the longitudinal axis L with respect to the housing 12 by a user to set the desired dose of medicament to be ejected from the injection device. The housing 12 includes an aperture 12a through which a dose indicator 18 is visible.

Figure 2:
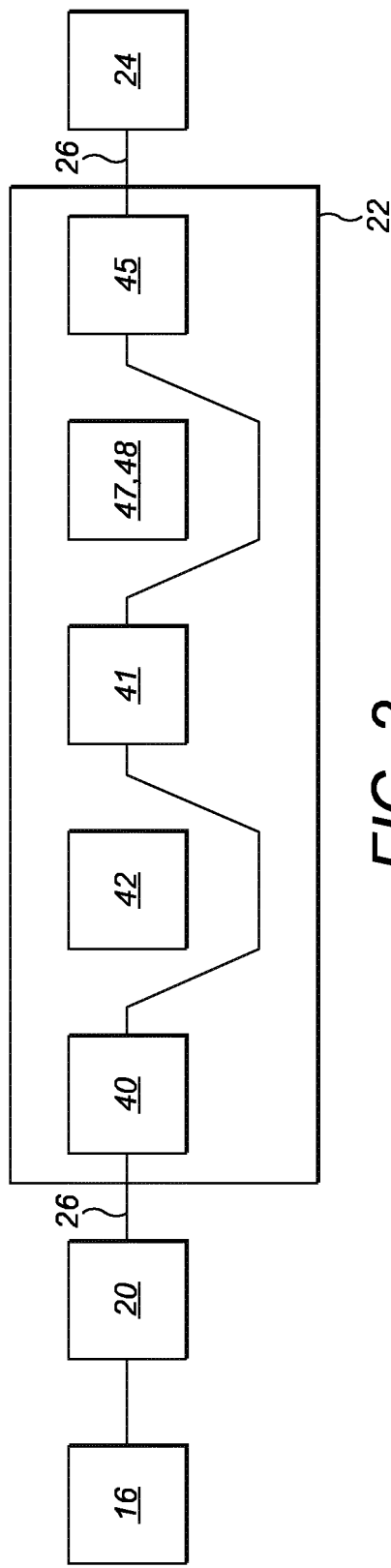
FIG. 2 is a schematic representation of components and a force path of the injection device of FIG. 1, with the dose limiting features disengaged.

FIG. 2 shows a schematic representation of a force path 26 within the injection device 10. The internal components include the dose selector 16, a spring 20, a drive assembly 22 and a medicament container 24. The drive assembly 22 includes a drive shaft 40, a last dose rotary endstop 42, a dose limit nut 41, dose limiting endstops 47, 48 and a plunger element 45. The spring 20 is configured to provide a drive force to the drive assembly 22 such that the drive assembly 22 may act to dispense medicament from the medicament container 24.

The dose selector 16 is coupled to the spring 20 such that a charging force can be transmitted via the force path 26 from the dose selector 16 to the spring 20 in order to charge the spring 20. The spring 20 is charged when a force is applied to the spring 20 so as to elastically deform the spring 20, and the resulting elastic energy is stored by the spring 20 (i.e. it is prevented from elastically relaxing during a storage phase). Therefore, charging the spring 20 involves increasing the energy stored by the spring 20.

The spring 20 is coupled to the drive assembly 22 and is arranged to provide a driving force via the force path 26 thereto when energy stored by the spring 20 is released. The spring is capable of storing energy necessary for ejecting the dose of medicament from the injection device.

The drive assembly 22 acts to expel medicament from the medicament container 24 using the plunger element 45 which is capable of providing an axial force for ejecting a dose of medicament from the container 24. In certain embodiments, the medicament container 24 may be a pre-filled syringe or cartridge having a barrel and a stopper moveable in the barrel. In such embodiments, the plunger element 45 may act to move the stopper so as to expel medicament through an opening in the barrel. In certain embodiments of the invention, the medicament cartridge may or may not be connected to a needle.

In embodiments where the spring 20 is a torsion spring, the spring 20 is charged by applying a torque to wind the spring 20 and elastic energy may be stored by the spring 20 and subsequently released as torque.

In embodiments where the spring 20 is a compression spring, the spring 20 may be charged by applying an axial force to compress the spring 20 and elastic energy may be stored by the spring 20 and subsequently released as an axial force.

The drive spring 20 when implemented as a torsion spring may be fixed at one end with respect to the housing 12 and rotationally coupled at its other end to the drive shaft 40 of the drive assembly 22.

In certain embodiments, the force path 26 may include one or more torque paths and/or one or more axial force paths, where one or more rotational to axial couplings are employed to switch between rotational and axial forces along the force path 26. Indeed, in certain embodiments, one or more intermediate components may be provided between any of the components shown in FIG. 2.

The drive shaft 40 and dose limit nut 41 are rotationally coupled together but are able to move axially with respect to one another. As shown in FIG. 2, as the drive shaft 40 is rotated, force is transmitted along the force path 26 to the dose limit nut 41 which therefore also rotates. The last dose rotary endstop 42 is not engaged (and is therefore not part of the force path 26) in FIG. 2.

The plunger element 45 is threaded so that the dose limit nut 41 is engaged with said plunger element 45 via said thread, in order to guide relative axial movement between the dose limit nut 41 and the plunger element 45. The dose limit nut 41 is provided with dose limiting endstop features 47, 48 which are capable of limiting axial travel of the dose limit nut 41 with respect to the plunger element 45, so as to limit maximum and minimum doses of medicament which can be set by the user. The dose limiting endstop features 47, 48 may engage with changes in the depth of the plunger element thread or formations on the thread, for example. The dose limiting endstop features 47, 48 are not engaged in FIG. 2 (and are therefore not part of the force path 26).

Maximum/Minimum Dose Limiting

As the drive shaft 40 is rotated during dose setting, the dose limit nut 41, which is rotationally coupled with the drive shaft 40, is also rotated. The dose limit nut 41 travels forwards along the plunger element thread when incrementing the dose and rearwards when decrementing the dose. When one of the dose limiting endstop features 47, 48 engages, the dose limit nut 41 cannot travel further in that axial direction. Axial travel of the dose limit nut 41 along the plunger element 45 during dose setting is only possible within a range determined by the dose limiting endstop features 47, 48. The dose limit nut 41 always remains within this range because, during dose delivery, the dose limit nut 41 does not move axially with respect to the plunger rack 45.

Limiting the travel of the dose limit nut 41 in this way sets the maximum and minimum doses of medicament that can be set during dose setting, for example 100 IU and 0 IU respectively.

Figure 3:
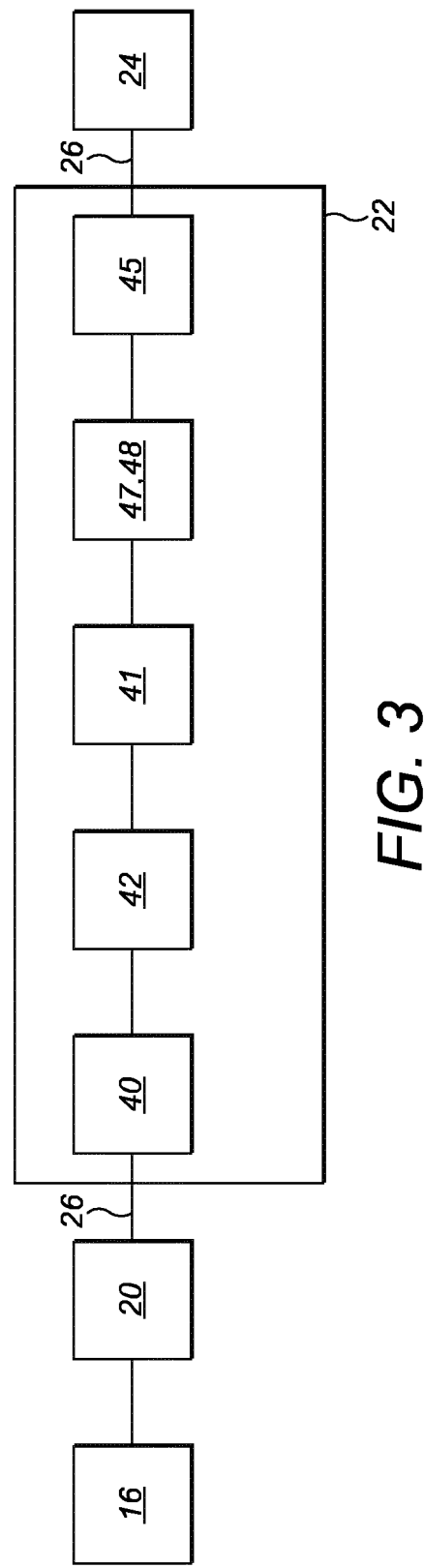
FIG. 3 is a schematic representation of components and a force path of the injection device of FIG. 1, with the dose limiting features engaged.

FIG. 3 shows the condition in which one of the dose limiting endstops 47, 48 is engaged and is now part of the force path 26 between the dose limit nut 41 and the plunger element 45.

Last Dose Protection

When the medicament cartridge 24 is relatively empty, after several doses have already been delivered therefrom, it is undesirable for the user to be able to select a dose that is larger than the available quantity of medicament remaining. Last dose protection is provided to deal with this situation. Conveniently, the last dose protection is provided by the same component as the maximum/minimum dose limiting i.e. the dose limit nut 41.

During dose setting, if the user attempts to set a dose that is greater than the available injectable volume of medicament remaining in the container 24, the last dose rotary endstop feature 42 engages, as represented in FIG. 3. The last dose rotary endstop feature 42 prevents further attempted rotation of the dose limit nut 41 by the drive shaft 40 with which it is rotationally coupled. An over-torque feature (not illustrated) may be provided to offer an alternate or additional force path if the user continues to attempt to dial up the dose selector 16.

The dose limit nut 41 conveniently provides last dose protection and maximum/minimum dose limiting with a single component, reducing the total number of component parts required and simplifying the injection device's design.

Description of Second Example Embodiment

A further non-limiting embodiment of an injection device according to the present invention is illustrated in FIGS. 4-19B.

Figure 4:
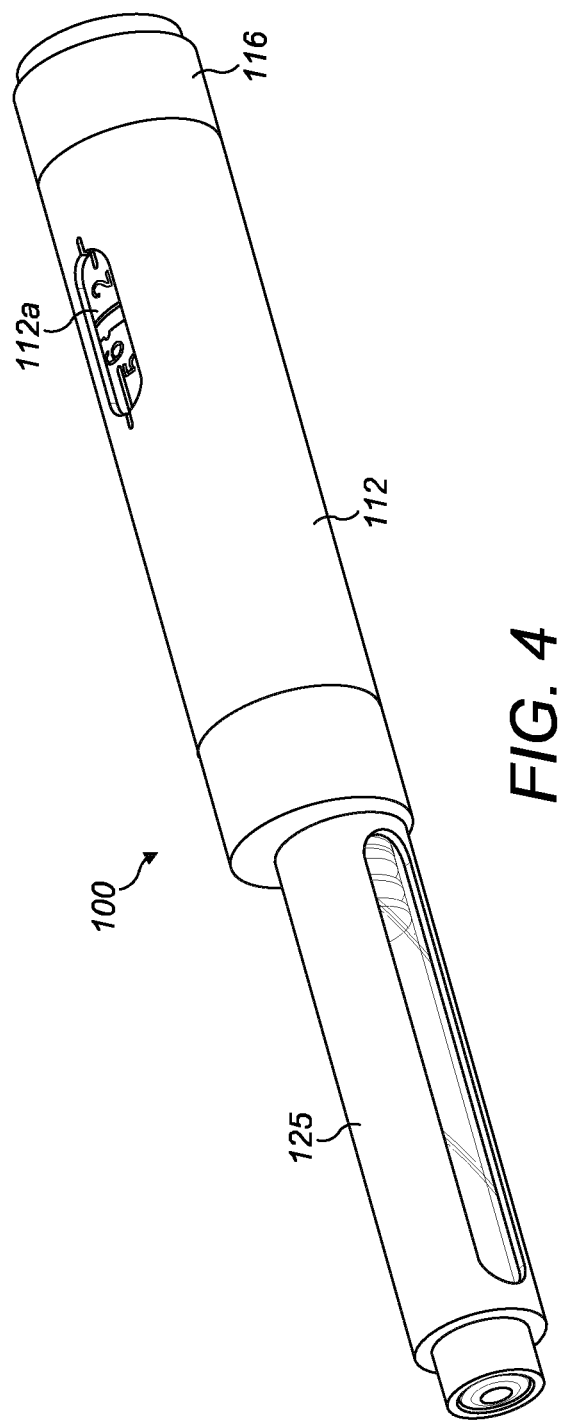
FIG. 4 is a perspective view of another embodiment of the injection device.
Figure 5:
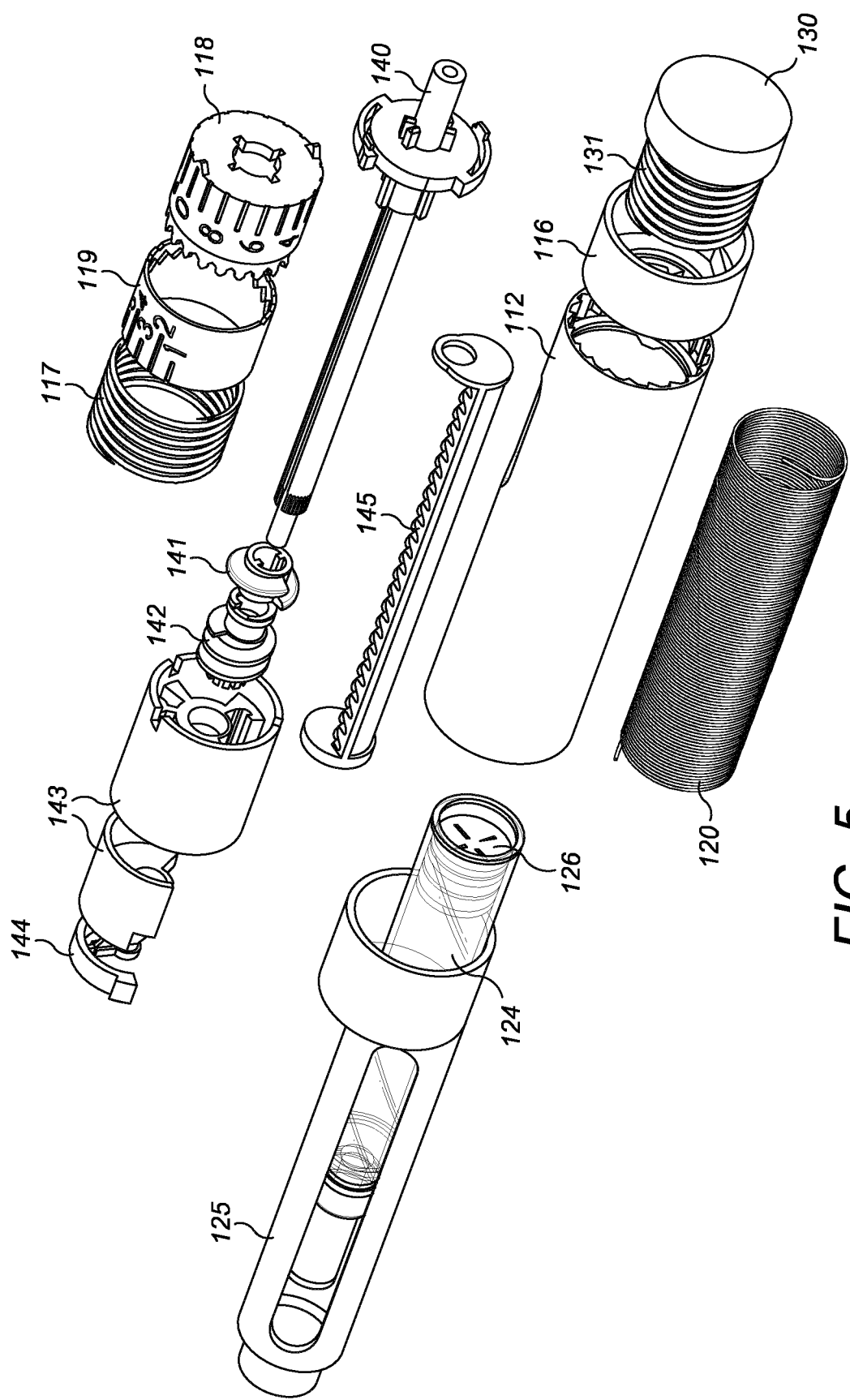
FIG. 5 is an exploded view of the injection device of FIG. 4.
Figure 6:
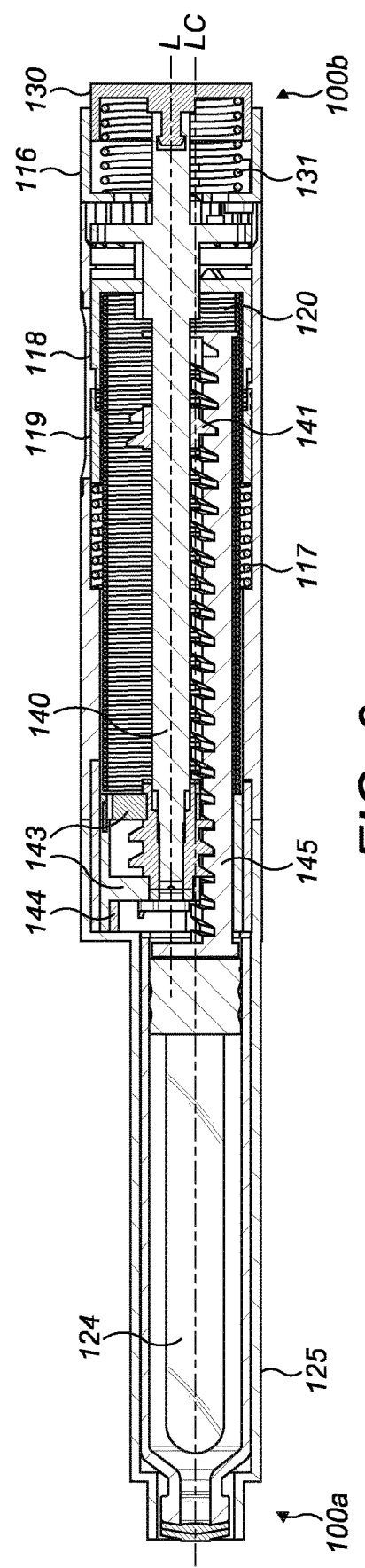
FIG. 6 is a cross-sectional view of the injection device of FIG. 4.

Referring to FIGS. 4-6, the injection device 100 includes a housing 112, a dose selector 116, a dose button 130 and dose button spring 131, a units wheel 118, a tens wheel 119, a dose indicator spring 117, a drive shaft 140, a drive spring 120, a dose limit nut 141, a worm gear 142, a worm gear support 143 and a worm gear rotational lock 144, all located concentrically about a common longitudinal axis L. The axis L extends between a front end 100a and a rear end 100b of the injection device 100.

The injection device 100 has a medicament cartridge 124 supported in a cartridge holder 125 at the front end 100a of the injection device 100. The cartridge 124 is sealed by an axially-moveable cartridge stopper 126 at its rear end. The cartridge and cartridge holder are located concentrically about a second longitudinal axis Lc, such that the cartridge is offset from the main housing 112, with L and Lc offset from one another as shown in FIG. 6.

The dose button 130 is biased rearwardly by the dose button spring 131. The dose selector 116 is provided at the rear end 100b of the injection device 100 and is arranged to permit the selection of a desired dose of medicament for delivery from the medicament cartridge 124 into an injection site. The dose selector 116 is axially constrained with respect to the housing 112 but is rotatable with respect thereto, about axis L. The dose selector 116 is rotationally coupled to the drive shaft 140 via pawl features 115, visible in FIG. 7A, which engage splines 149 on the drive shaft 140. The housing 112 is provided with teeth 113 (visible in FIG. 7B) on an inside surface thereof for engaging ratchet arms 146 on the drive shaft 140. Tabs 114 on the dose selector 116 are capable of depressing the drive shaft ratchet arms 146 when required, as shown in FIG. 8B. The housing 112 is also provided with ramp features 111 (visible in FIG. 12A) which facilitate disengagement of the ratchet arms 146 from the inside surface of the housing 112 when required.

A dose indicator is disposed within the housing 112 and displays reference indicia, such as numbers or symbols, to indicate the level of dose selected by the dose selector 116. The housing 112 includes an aperture 112a through which the dose indicator is visible. The dose indicator comprises the units wheel 118 for displaying units and the tens wheel 119 for displaying tens. The units wheel 118 is selectively engageable with the tens wheel to increment the tens wheel each time the units wheel moves through units 0 to 9. The units wheel 118 is rotationally coupled to the drive shaft 140.

As with the first embodiment, described with reference to FIGS. 1-3, biasing means in the form of dose indicator spring 117 biases the units wheel 118 and tens wheel 119 axially rearwardly in the housing.

The housing 112 has features on an inside surface thereof for engaging with the units wheel 118 and the tens wheel 119.

An internal surface of the housing 112 is provided with a tens housing feature 108 selectively engageable with the tens wheel 119 to prevent rotation thereof. The tens housing feature comprises one or more axially forwardly extending formations 108 which may be equally spaced around the internal circumference of the housing 112. The formations 108 engage with corresponding axially rearwardly extending formations 119b at the rear of the tens wheel 119. The tens housing feature formations 108 and the tens wheel formations 119b may be teeth, notches, castellations or any other shaped formations that, when engaged together, prevent relative rotation between the tens wheel 119 and the housing 112.

An internal surface of the housing 112 is provided with a units housing feature 107 capable of moving the units wheel axially-forward against said biasing means 117. The units housing feature is an axially forwardly extending formation 107 having a cam surface which can engage with an axially rearwardly extending formation 118b on the units wheel 118 in order to push the units wheel 118 axially forwards.

Teeth 118a on the front end of the units wheel 118 are engageable with correspondingly shaped teeth 119a at the rear end of the tens wheel 119. On the tens wheel 119, the teeth 119a (for engaging the units wheel) and the tens wheel formations 119b (for engaging the housing) may be concentrically arranged around the longitudinal axis of the injection device, with the teeth 119a radially inward of the formations 119b.

The drive spring 120 is a torsion spring which is fixed at one end with respect to the housing 112 and rotationally coupled at its other end to the drive shaft 140 via the units wheel 118.

A worm gear arrangement is provided which comprises a worm gear 142 meshed with a toothed plunger rack 145 located within the housing 112. During dose delivery, the worm gear 142 drives the plunger rack 145 forward which, in turn, pushes against the cartridge stopper 126 to deliver a dose of medicament. A splined clutch 150 at the forward end of the drive shaft 140 enables the worm gear 142 and drive shaft 140 to be splined together during dose delivery but not during dose setting, described in more detail later. In FIG. 6, the worm gear rotational lock 144 is engaged in the forward end of the worm gear 142, preventing rotation thereof. The worm gear rotational lock 144 is capable of being pushed axially forward by the drive shaft 140 in order to disengage the lock from the worm gear 142.

Figure 5B:
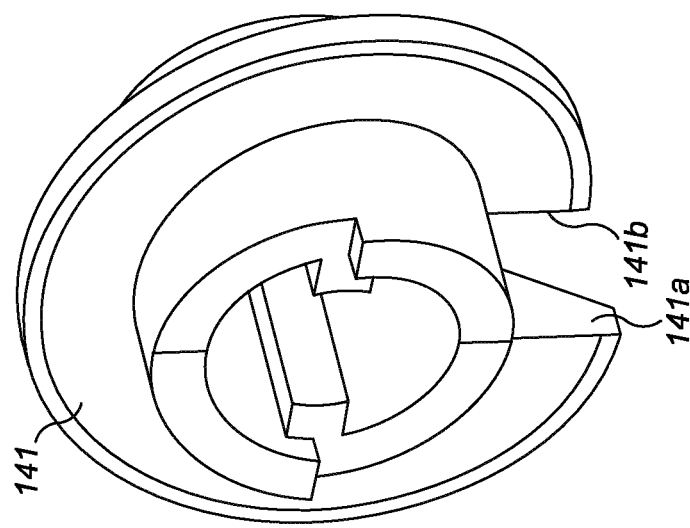
FIG. 5B is a perspective view showing further detail of part of the plunger rack.
Figure 5A:
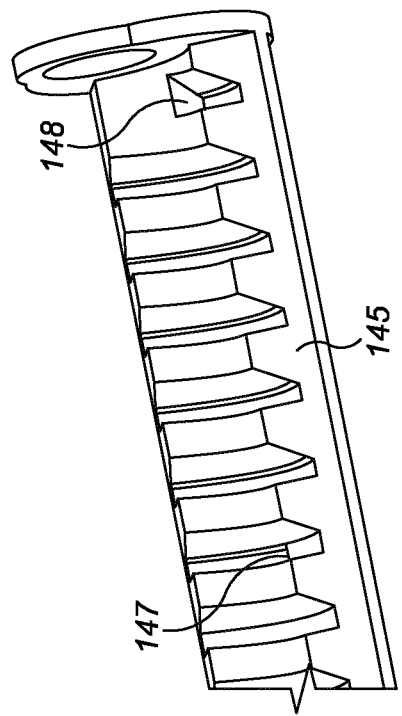
FIG. 5A is a perspective view showing further detail of the dose limit nut.

The dose limit nut 141 is keyed to the drive shaft 140 so that they are rotationally coupled but not axially coupled. The dose limit nut 141 is engaged with the teeth of the plunger rack 145 and can travel axially forward and backward along the plunger rack 145 as the dose is incremented or decremented respectively. The axial range within which the dose limit nut 141 can travel along the plunger rack 145 is determined by dose limit nut endstop features 141a, 141b which can engage features 147, 148 on the plunger rack thread to serve as endstops for the travel of the dose limit nut 141. FIG. 5A shows the maximum dose limit nut endstop feature 141a and the minimum dose limit nut endstop feature 141b in more detail. Endstops 141a, 141b are able to engage features 147, 148 respectively on the plunger rack 145 (FIG. 5B). These features 147, 148 are preferably changes in the depth of or formations on the plunger rack thread, past which the dose limit nut 141 cannot travel. During dose delivery, the dose limit nut 141 rotates about axis L with the drive shaft 140 to which it is keyed, but it does not move axially with respect to the plunger rack 145 with which it is engaged, thus always keeping the dose limit nut 141 within the range defined by the max/min dose endstops 141a, 141b.

The operation of the respective features of the injection device 100 will now be described in more detail below.

Dose Setting—Incrementing the Dose

Figure 7:
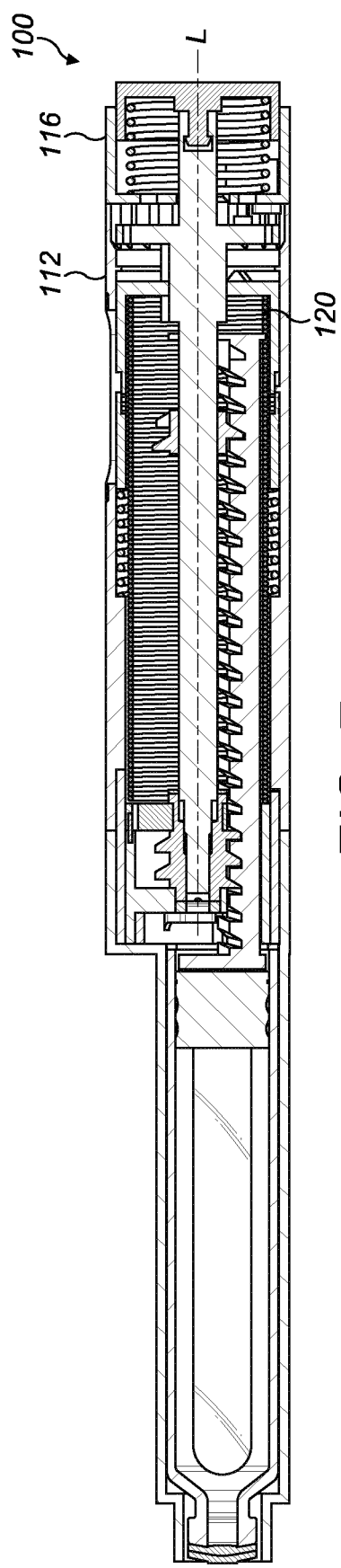
FIGS. 7 and 7A-7C illustrate incrementing the dose.
Figure 7C:
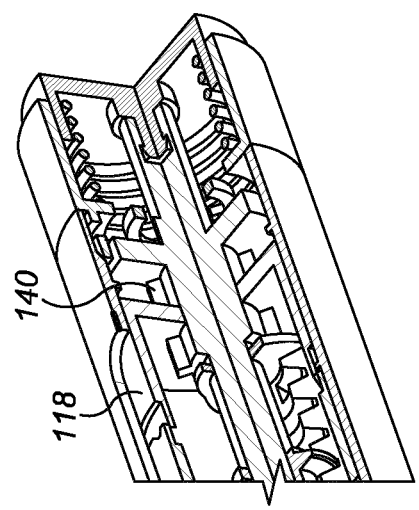

With the injection device 100 in the configuration shown in FIG. 7, the user grips the dose selector 116 and rotates it clockwise about axis L, with respect to the housing 112, in order to increment the dose and charge the drive spring 120. As the dose selector 116 is turned clockwise, the pawl features 115 engaging the splines 149 on the drive shaft 140 cause the drive shaft 140 to also be driven clockwise, as shown in FIG. 7A.

Figure 7B:
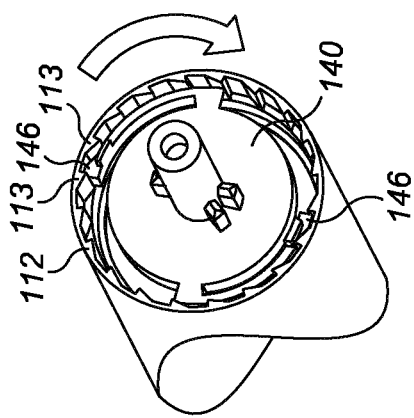
Figure 7A:
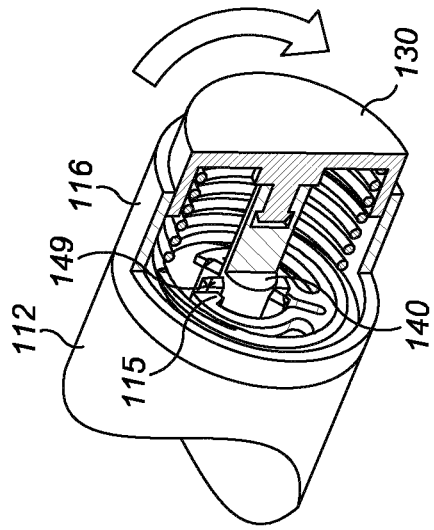
Figure 8:
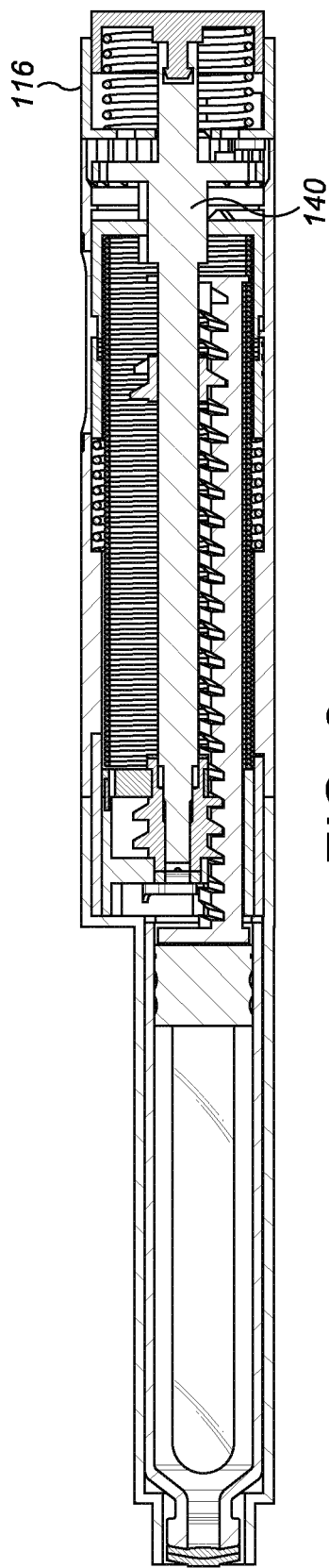
FIGS. 8, 8A and 8B illustrate decrementing the dose.
Figure 8B:
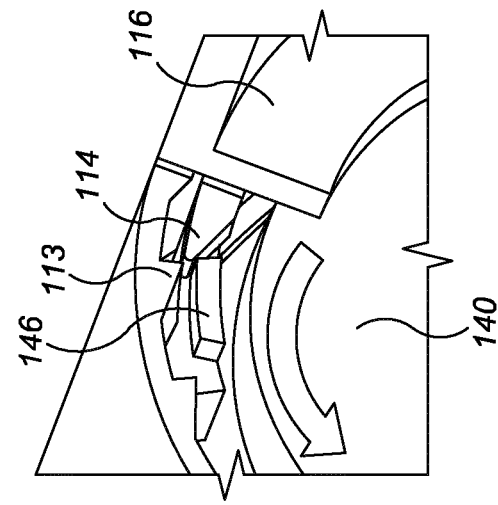

While the dose is being incremented, the ratchet arms 146 on the drive shaft 140 engage with the teeth 113 on the inside surface of the housing 112 to prevent un-winding by the drive spring 120, as shown in FIG. 7B.

As shown in FIG. 7C, the drive shaft 140 is splined to the units wheel 118 which charges or torques up the drive spring 120. In other words, torque is transferred from the dose selector 116 to the drive spring 120 directly through the dose indicator, i.e. the units wheel 118.

Dose Setting—Decrementing the Dose

Figure 8A:
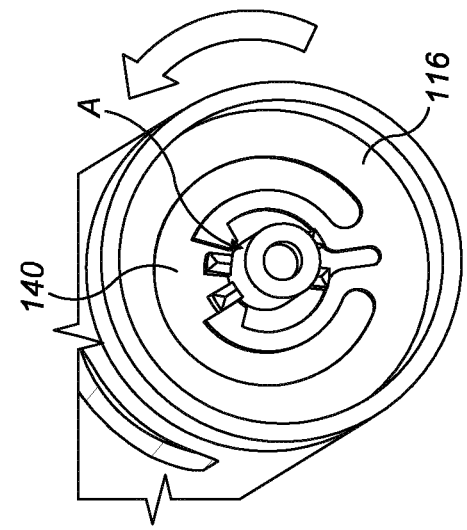

When it is desired to decrement the selected dose, the dose selector 116 is turned anti-clockwise. As shown in FIG. 8A, as the dose selector 116 is turned anti-clockwise, there is a small amount of backlash at point A such that the dose selector 116 can rotate slightly with respect to the drive shaft 140. This small relative movement is sufficient to allow the tabs 114 on the dose selector 116 to depress the drive shaft ratchet arms 146 so that they can click past the housing teeth 113, allowing the drive spring to unwind slightly before the ratchet arms 146 catch again on the next housing tooth 113. This is represented in FIG. 8B. Each decrement preferably equates to 1 IU ("international unit") of medicament.

Dose Setting—Maximum/Minimum Dose

Figure 9:
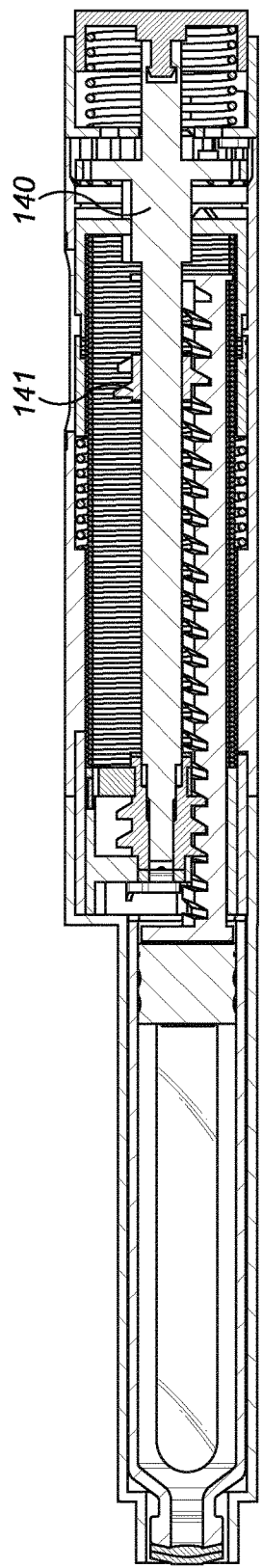
FIGS. 9, and 9A-9D illustrate maximum/minimum dose limiting.
Figure 9C:
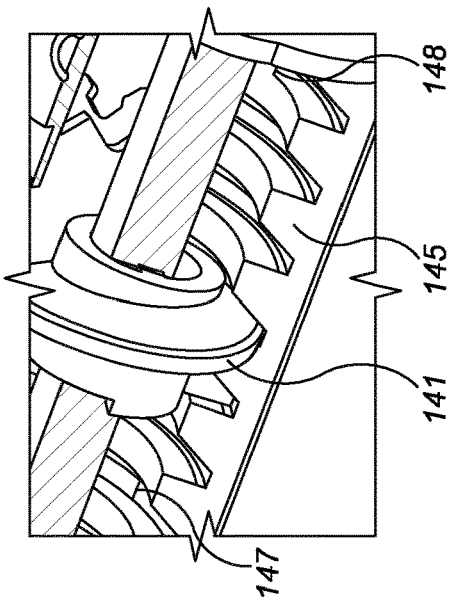
Figure 9B:
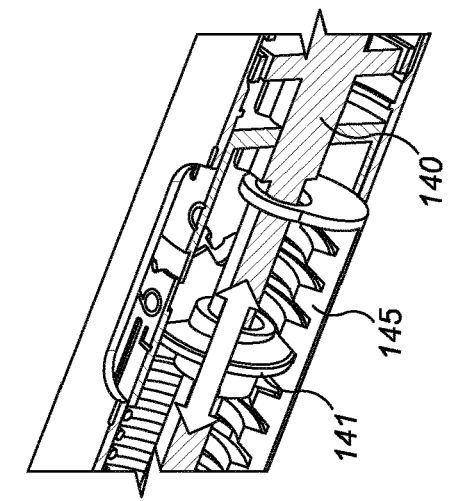
Figure 9A:
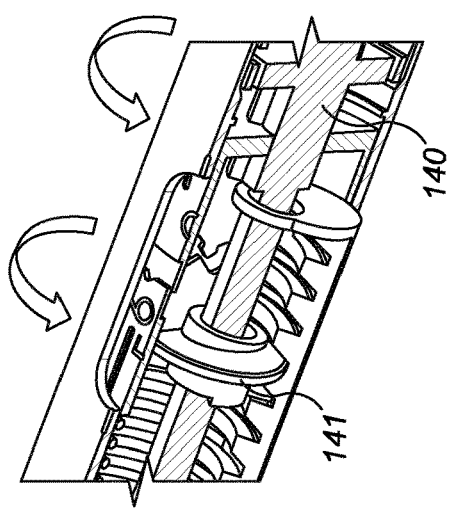
Figure 9D:
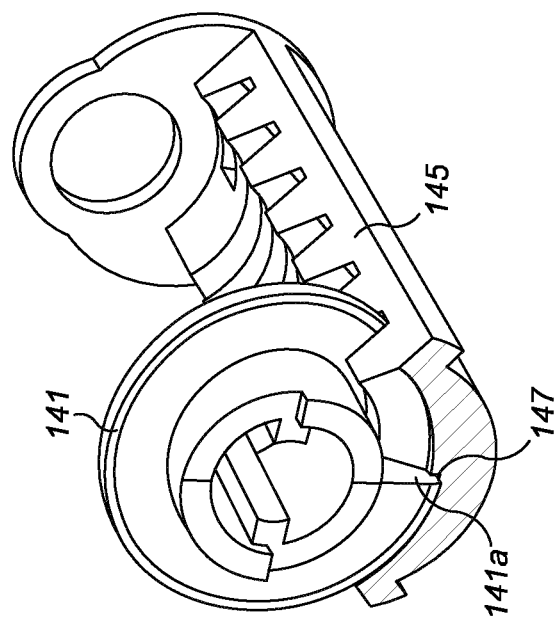

As the drive shaft 140 is rotated during dose setting, the dose limit nut 141, which is keyed to the drive shaft 140, is also rotated (FIG. 9A). The dose limit nut 141 travels forwards when incrementing the dose and rearwards when decrementing the dose (FIG. 9B). The dose limit nut 141 is engaged in the thread of the plunger rack 145. Endstop features 147, 148 are located on the plunger rack 145, past which the dose limit nut 141 cannot travel (FIG. 9C). These endstop features 147, 148 may be changes in the depth of the thread. As shown in FIG. 9D, when the dose limit nut 141 rotates into a position wherein the dose limit nut endstop feature 141a engages feature 147 on the plunger rack 145, further rotation of the dose limit nut 141 is prevented so that a dose of medicament greater than the desired maximum dose of medicament cannot be set. Limiting the travel of the dose limit nut 141 sets the maximum and minimum doses of medicament that can be set during dose setting, preferably 100 IU and 0 IU respectively.

Dose Setting—Over Torque

Figure 10:
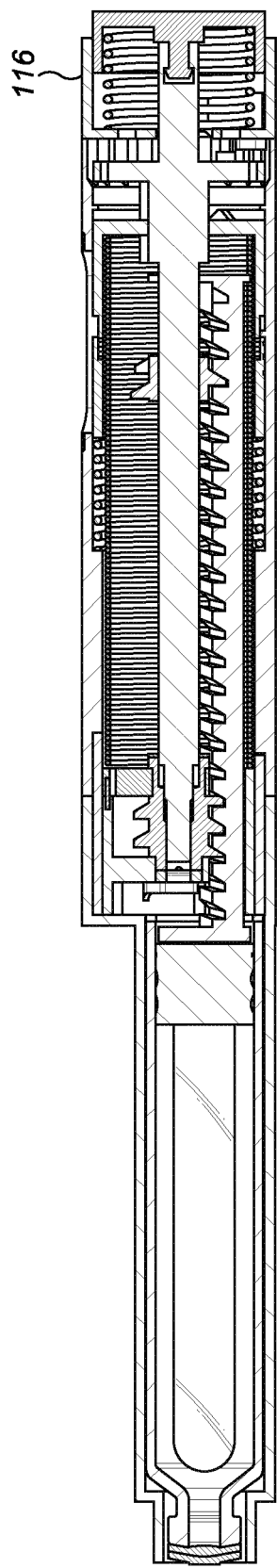
FIGS. 10 and 10a illustrate over-torque protection.
Figure 10A:
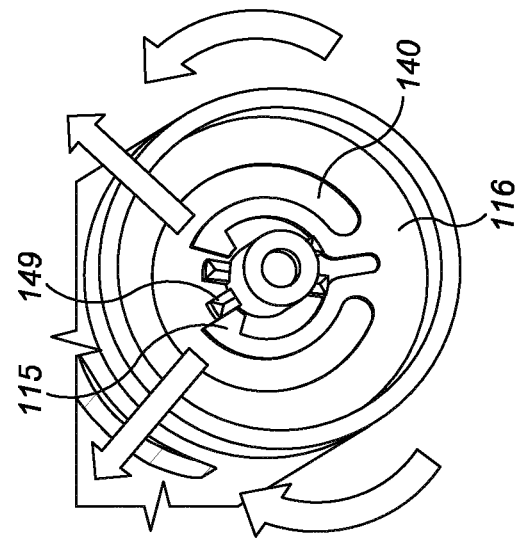

As shown in FIG. 10A, in the event the user applies too much force (over torque) to the dose selector 116 in either rotational direction, the dose selector pawl features 115 will flex radially outwardly to allow them to skip past splines 149 on the drive shaft 140. Preferably the interfacing surface areas of the pawl features 115 and/or splines 149 act as a cam lever, preferably having a matching angle and/or a defined static and dynamic surface friction at the interface surface. The over-torque for flexing out the dose pawl features 115 to skip past spline 149 is preferably at least 10% higher than the torque required for dialing up (incrementing) or dialing down (decrementing) the dose indicator 18, 118. The dialing up torque can be 30 to 80 Nmm, preferably less than 60 Nmm, more preferably 30 to 50 Nmm. The dialing down torque can be 20 to 60 Nmm, preferably less than 50 Nmm, more preferably 30 to 40 Nmm. The over-torque in the dialing up direction may be different to the over-torque in dialing down direction. The outward flexing force and/or strength of one flexible pawl arm 115 could be lower compared to a second flexible pawl arm.

Figure 16:
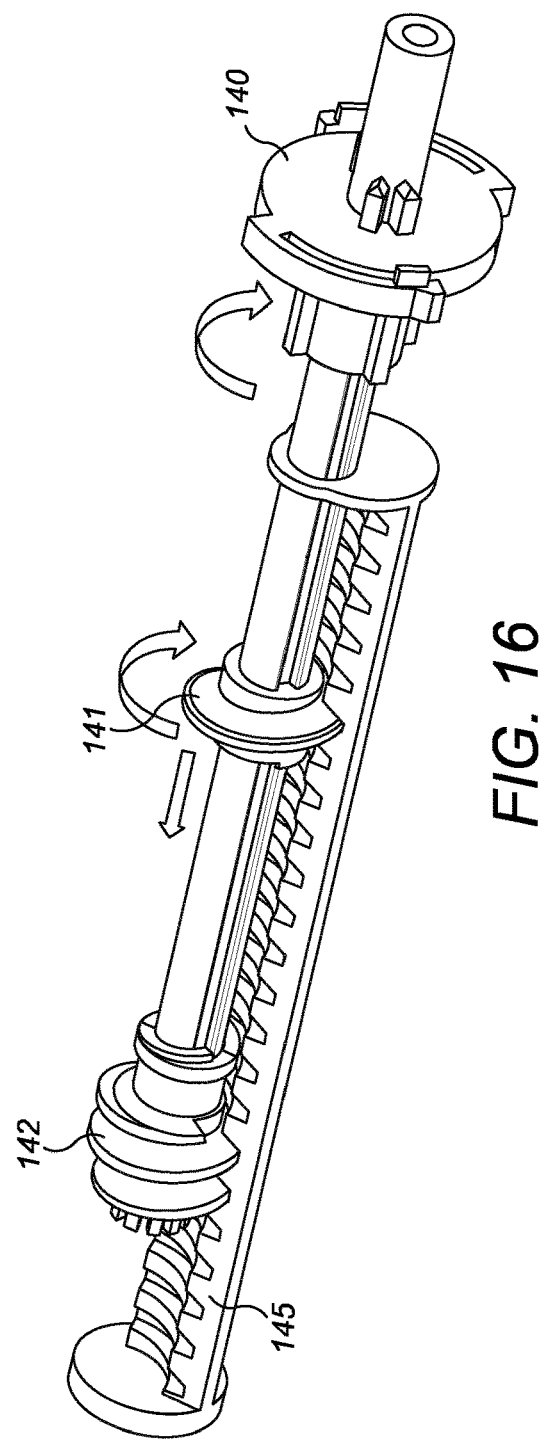
FIG. 16 summarises schematically the mechanical motion of the drive shaft 140, dose limit nut 141, worm gear 142 and plunger rack 145 during dose setting (incrementing the dose)

FIG. 16 summarises schematically the mechanical motion of the drive shaft 140, dose limit nut 141, worm gear 142 and plunger rack 145 during dose setting (incrementing the dose). The drive shaft 140 rotates clockwise. The dose limit nut 141 rotates clockwise and advances forwards with respect to the plunger rack 145.

Dose Delivery

To initiate dose delivery, the user presses the dose button 130 against the bias of the dose button spring 131 as shown in FIG. 11A. This pushes the drive shaft 140 axially forwards. Although the drive shaft 140 is splined to the units wheel 118, it is free to slide axially with respect thereto (FIG. 11B).

Figure 12:
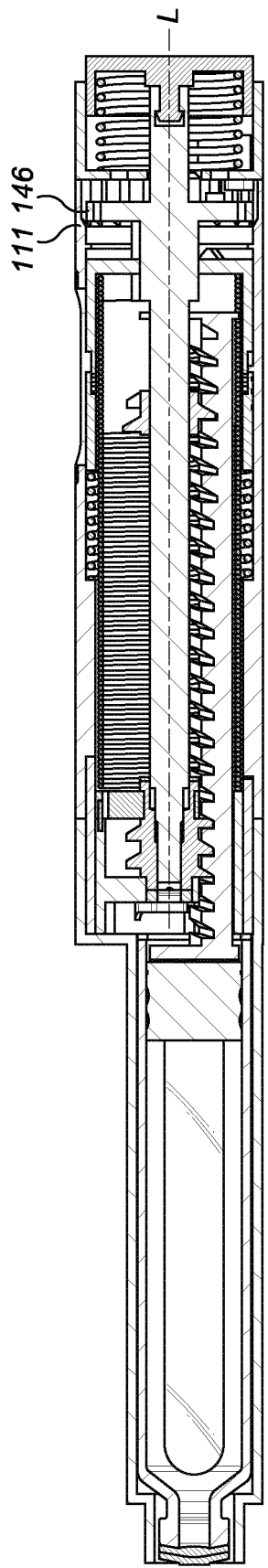
Figure 12B:
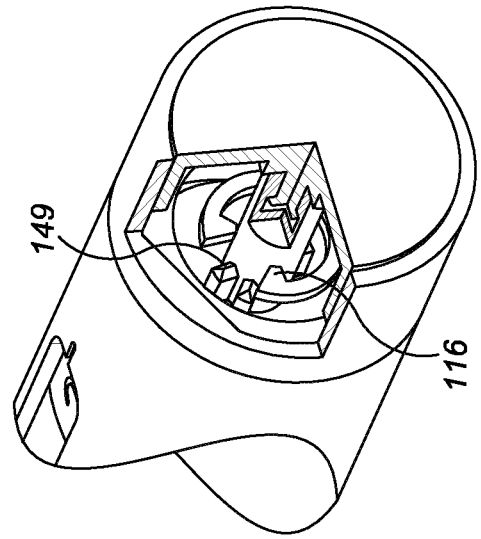
Figure 12A:
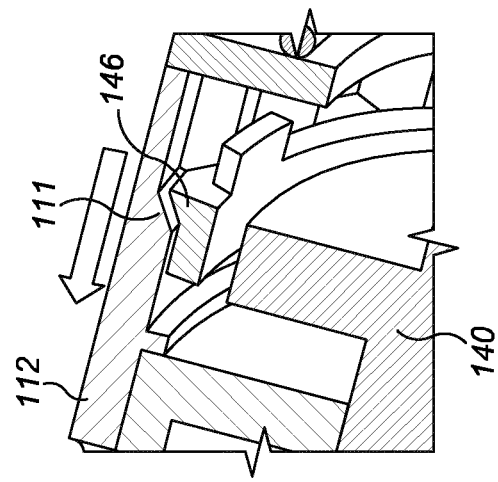
Figure 15:
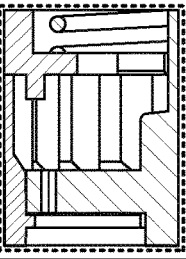
FIG. 15 is a diagrammatic summary of the key engagement points of the components of the injection device of FIG. 4, at four stages of dose delivery.

As the drive shaft 140 advances, at its forward end, the splined clutch 150 between the drive shaft and the worm gear 142 engages (FIG. 11C, FIG. 15—Worm Gear Clutch 150). Preferably the drive element, in particular the worm gear 142 and the drive shaft 140 engage after 0.5 mm to 1.5 mm advancement of the dose button 130, more preferably after 0.8 mm to 1.2 mm advancement of the dose button 130. Once the clutch 150 has started to engage, the ratchet arms 146 on the drive shaft 140 begin to disengage from the inside surface of the housing 112 aided by ramp features 111 (FIG. 12A, FIG. 15—Hold Ratchet). Preferably the hold ratchet, in particular the ratchet arms 146 on the drive shaft 140 start to disengage from the structured, in particular toothed surface of the housing 112 after 1.5 mm to 2.5 mm advancement of the dose button 130, more preferably after 1.6 mm to 1.9 mm advancement of the dose button 130. Also, as the drive shaft 140 moves forward, the splines 149 coupling the drive shaft 140 to the dose selector 116 disengage (FIG. 12B, FIG. 15—Over torque ratchet). Preferably the over torque ratchet, in particular the drive shaft splines 149 on the drive shaft 140 start to disengage from the dose selector pawls 115 after 1.5 mm to 3.5 mm of advancement of the dose button 130, more preferably after 2 mm to 3 mm advancement of the dose button 130. The dose indicator and drive shaft 140 are now free to rotate about longitudinal axis L.

The drive spring 120 drives the units wheel 118 to rotate about longitudinal axis L. The units wheel 118 drives the drive shaft 140 which drives the worm gear 142.

Figure 17:
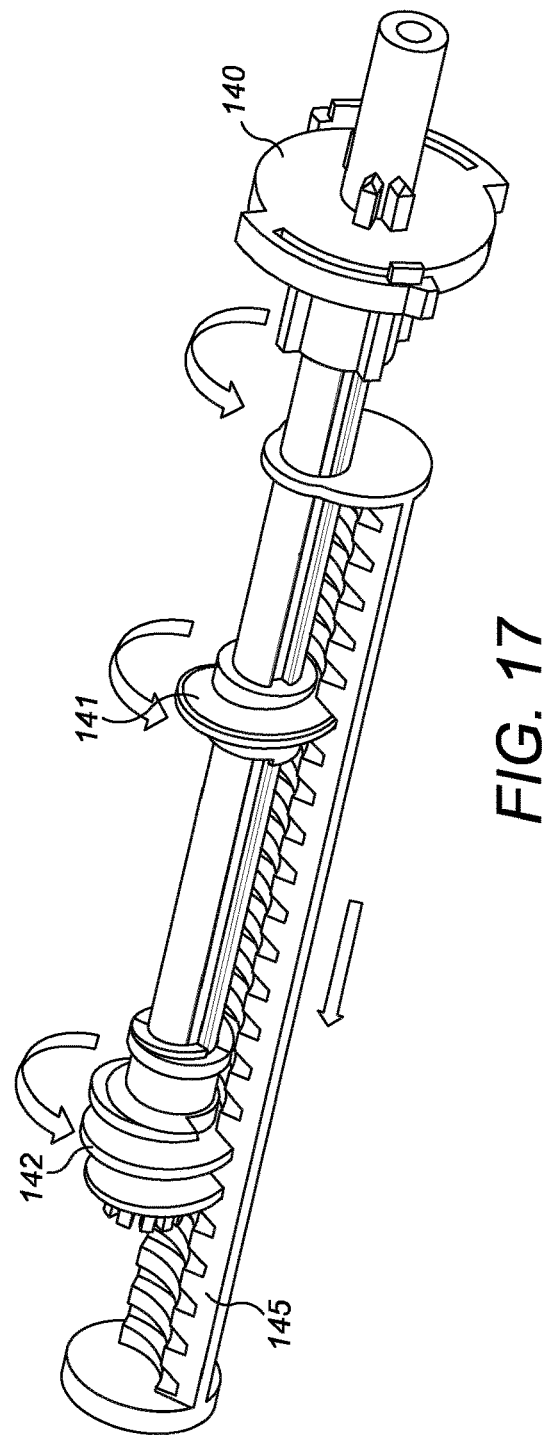
FIG. 17 summarises schematically the mechanical motion of the drive shaft 140, dose limit nut 141, worm gear 142 and plunger rack 145 during dose delivery.

FIG. 17 summarises schematically the mechanical motion of the drive shaft 140, dose limit nut 141, worm gear 142 and plunger rack 145 during dose delivery. The drive shaft 140, dose limit nut 141 and worm gear 142 all rotate anti-clockwise. Only the plunger rack 145 advances forwards. During dose delivery, the dose limit nut 141 rotates with the drive shaft 140 but does not move axially with the plunger rack 145. The dose limit nut 141 and the drive worm gear 142 preferably have the same thread pitch.

The worm gear 142 actuates the plunger rack 145 to move axially forwards causing the cartridge stopper 126 to be driven into the cartridge in order to expel medicament thus delivering the selected dose.

When the dose button 130 is released, the dose button spring 131 returns the dose button 130 and drive shaft 140 to their original starting positions. This axially rearward movement disengages the worm gear clutch 150 and re-engages the drive shaft ratchet arms 146 with the housing 112 thereby stopping dose delivery.

Dose Delivery—Haptic Feedback

Figure 13:
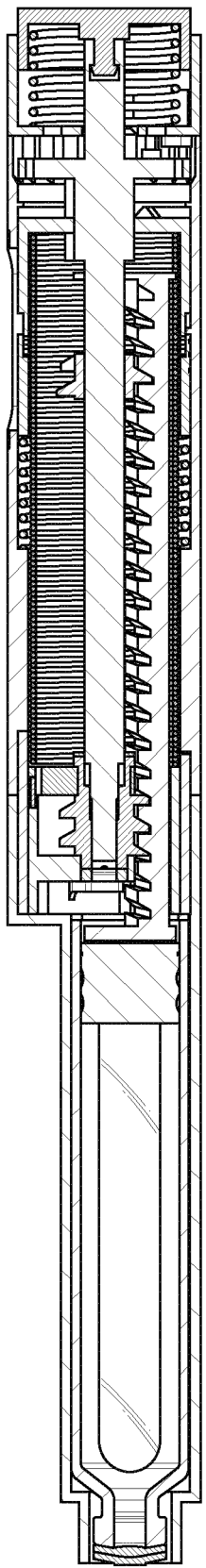
FIGS. 13, 13A and 13B illustrate a haptic feedback feature.
Figures 13A, 13B:
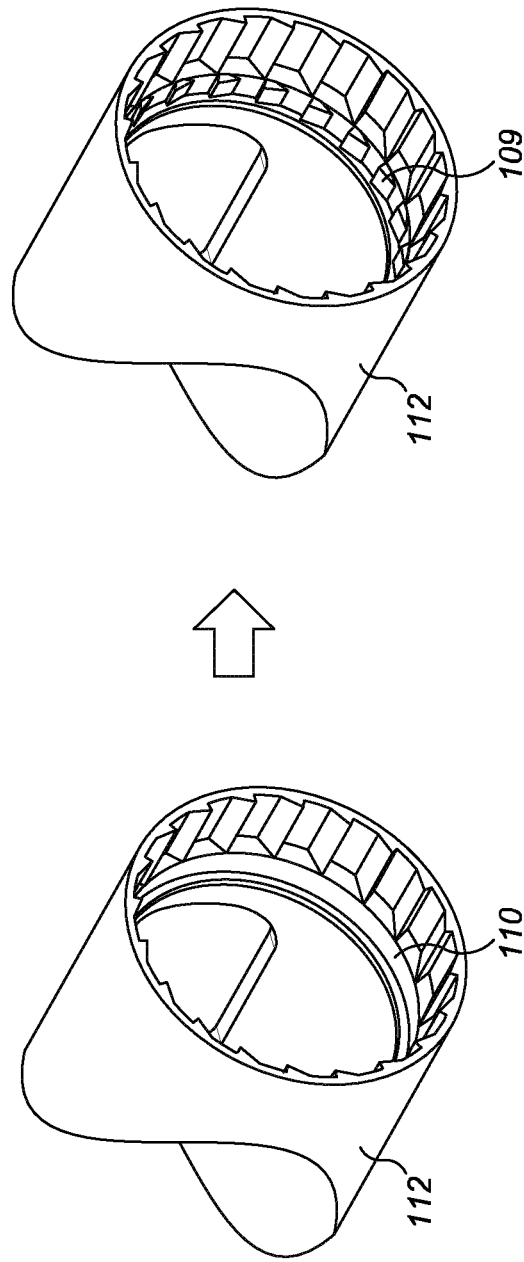

During dose delivery, the drive shaft ratchet arms 146 run (rotationally) on a relatively smooth track 110 on the inside surface of the housing 112 (FIG. 13A). Optionally, this track could be modified to include ridges 109 which would provide audible/haptic feedback to the user during dose delivery (FIG. 13B). The ridges 109 are conveniently placed relatively close to the user's fingers.

Last Dose Protection

When the medicament cartridge 124 is relatively empty, after several doses have already been delivered therefrom, it is undesirable for the user to be able to select a dose that is larger than the available quantity of medicament remaining. Last dose protection is provided to deal with this situation. Conveniently, the last dose protection is provided by the same feature as the max/min dose limiting i.e. the dose limit nut 141.

As shown in FIG. 14, after several doses have been delivered, the plunger rack 145 and dose limit nut 141 have advanced axially forwards such that the dose limit nut 141 is approaching the worm gear 142. When there is less than a predetermined amount (e.g. 100 IU) of medicament available, the worm gear 142 serves as an endstop, stopping the dose limit nut 141 from moving further forwards and before the maximum dose limit feature 147 on the plunger rack 145 is reached (FIG. 14A). Preferably, it is the dose limit nut endstop feature for maximum dose limiting 141a which engages the worm gear 142. If the user tries to increment the dose further, torque is transmitted through the dose limit nut 141 into the worm gear 142, the torque being reacted to by the worm gear rotational lock 144 (FIG. 14B). As such, the worm gear 142 is unable to rotate due to rotational engagement with the rotational lock 144.

Figure 14C:
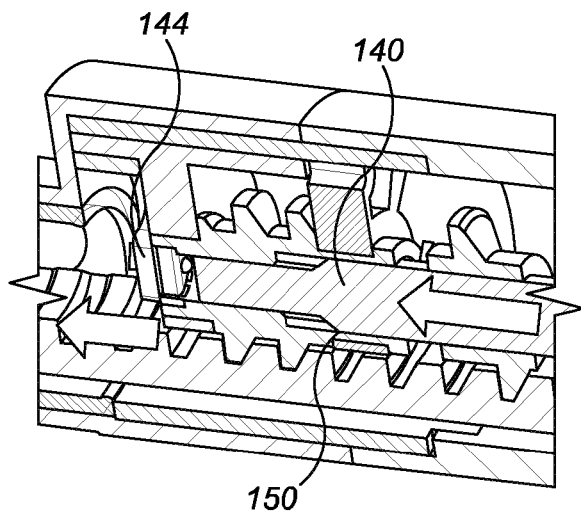
Figure 14D:
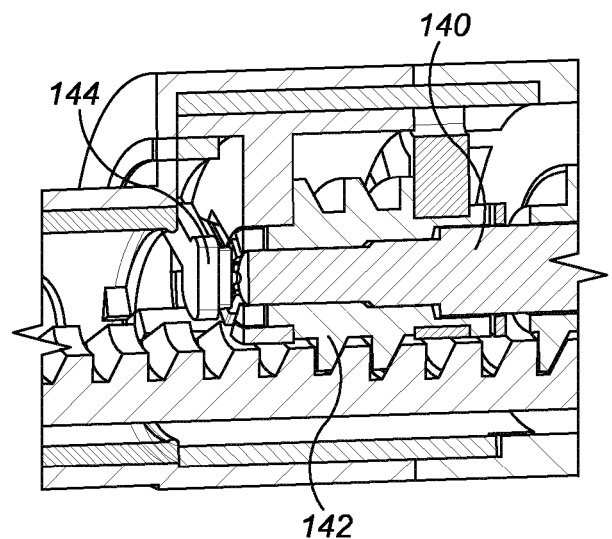
Figure 14E:
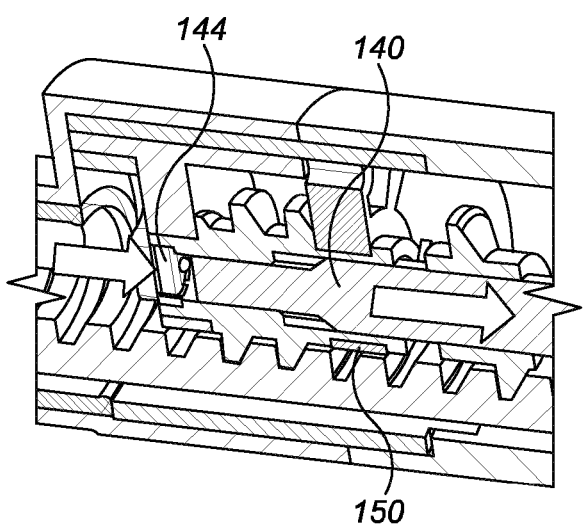

During dose delivery, when the drive shaft 140 is moved axially forwards, the worm gear clutch 150 is engaged before the worm gear rotational lock 144 is disengaged (FIG. 14C). The axially-forward movement of the drive shaft 140 causes its forward end to push the worm gear rotational lock 144 out of the front of the worm gear 142. With the worm gear rotational lock 144 disengaged, the worm gear 142 is free to rotate, driven by the drive shaft 140 (FIG. 14D). Once dose delivery is finished, the drive shaft 140 moves rearwardly. The worm gear rotational lock 144 re-engages, before the worm gear clutch 150 is disengaged (FIG. 14E).

FIG. 15 is a diagrammatic summary of the key engagement points of the injection device components, at four stages of dose delivery.

Dose Display

Figure 18:
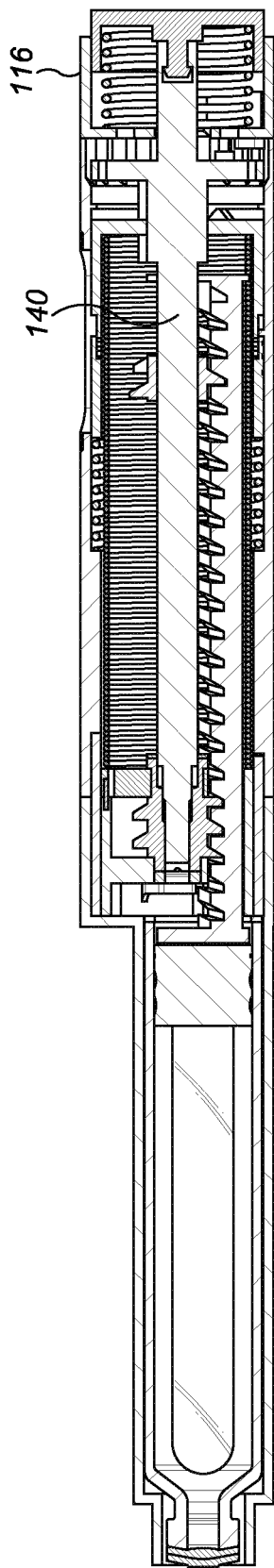
FIGS. 18, 18A and 18B show how the units wheel is incremented.
Figure 18B:
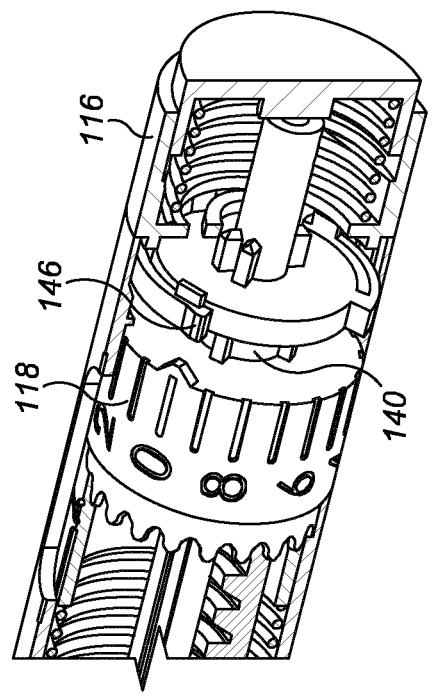
Figure 18A:
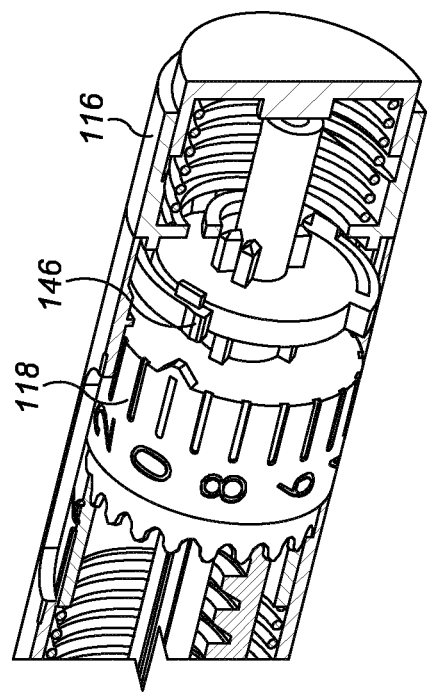

As already described above, during dose selection the user rotates the dose selector 116 which also drives the drive shaft 140 around. Ratchet arms 146 interact with teeth 113 in the housing 112 to prevent unwinding (FIG. 18A). The drive shaft 140 is splined to the units wheel 118 which, as it turns, increments the displayed unit (FIG. 18B).

Figure 19:
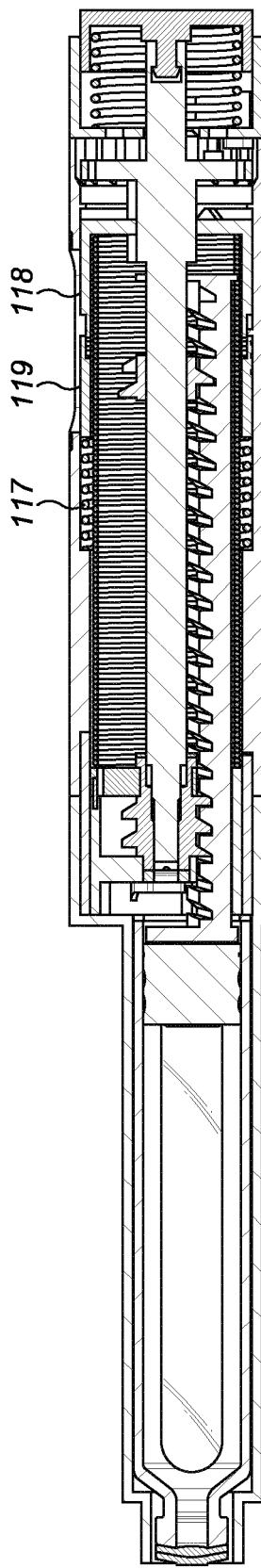
FIGS. 19, 19A and 19B show how the tens wheel is incremented.
Figure 19B:
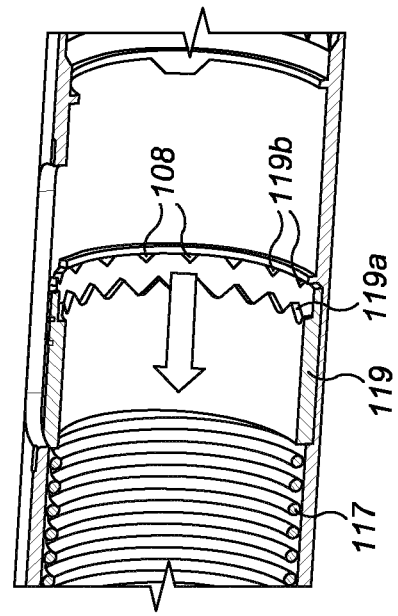
Figure 19A:
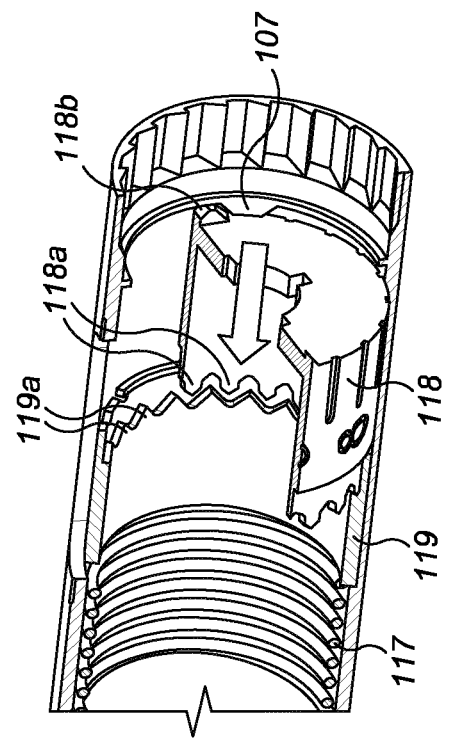

The units wheel 118 and tens wheel 119 are biased rearwardly by dose indicator spring 117. Twice per revolution of the units wheel 118, the units wheel 118 is moved axially forwards by the cam surface of the units housing feature 107 engaging with the formation 118b on the units wheel 118. This axially forward movement causes the teeth 118a of the units wheel 118 to engage with the teeth 119a of the tens wheel 119 (FIG. 19A). Continued forward axial movement of the units wheel 118 pushes the formations 119b of the tens wheel 119 away from the tens housing feature 108, so that the tens wheel 119 is free to rotate with respect to the housing 112, allowing the tens wheel 119 to be driven around by the units wheel 118 by one increment (FIG. 19B).

In a preferred embodiment, the selectable and settable dose range is 1 to 100 IU, with a minimum dose setting of 1 IU, wherein per 360 degree rotation of the dose selector 116, 20 to 30 IU may be set. As the units wheel 118 and tens wheel 119 arrangement permits indication of the set IU dose by two digits, a much larger font size for the indicated dose number is usable, thus the arrangement affords better readability of the set dose and usability of the injection device 10, 100.

As with the first embodiment, described with reference to FIGS. 1-3, a dose limit nut 141 and a plunger element (plunger rack 145) are each threaded so that the dose limit nut 141 is engaged with said plunger element 145 via said thread, in order to guide relative axial movement between the dose limit nut 141 and the plunger element 145.

The thread is provided with dose limiting endstops 147, 148 which are capable of limiting axial travel of said dose limit nut 141 with respect to said plunger element 145, so as to limit maximum and minimum doses of medicament which can be set by the user.

The dose limit nut 141 is also engageable with a last dose rotary endstop (worm gear 142) which prevents further rotation of the dose limit nut 141 with respect to the drive shaft 140 so as to prevent the user setting a dose that is greater than an injectable volume of medicament remaining in said medicament container.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 10 injection device
L longitudinal axis
10a front end of the device
10b rear end of the device
12 housing
14 needle
16 dose selector
18 dose indicator
20 spring
22 drive assembly
24 medicament container
26 force path
40 drive shaft
41 dose limit nut
42 last dose rotary endstop feature
45 plunger element
47, 48 dose limit nut endstop features
100 injection device
L longitudinal axis (housing)
Lc second longitudinal axis (cartridge)
100a front end of the device
100b rear end of the device
107 units housing feature
108 tens housing feature
109 housing ridge features
110 housing smooth inside surface track
111 housing ramps for drive shaft ratchet arms
112 housing
112a aperture in the housing
113 housing teeth
114 tabs
115 dose selector pawl
116 dose selector
117 dose indicator spring
118 units wheel
118a teeth on units wheel (for engaging tens wheel)
118b formation on units wheel (for engaging units housing feature)
119 tens wheel
119a teeth on tens wheel (for engaging units wheel)
119b formations on tens wheel (for engaging tens housing feature)
120 drive spring
124 medicament cartridge
125 cartridge holder
126 cartridge stopper
130 dose button
131 dose button spring
140 drive shaft
141 dose limit nut
141a dose limit nut endstop feature for max dose limiting and last dose limiting
141b dose limit nut endstop feature for min dose limiting
142 worm gear
143 worm gear support
144 worm gear rotational lock
145 plunger rack
146 drive shaft ratchet arms
147 max dose endstop on plunger rack for dose limit nut
148 min dose endstop on plunger rack for dose limit nut
149 drive shaft splines
150 worm gear clutch
A backlash point for over-torque protection

The invention claimed is:

1. An injection device comprising:
   a. a dose selector, rotatable by a user to set a dose to be ejected from the injection device
   b. a drive assembly including a drive shaft and a plunger element configured to move a stopper so as to expel medicament through an opening in a medicament container, the drive assembly being capable of providing an axial force for ejecting a dose of medicament from the medicament container,
   c. a dose limit nut rotationally coupled to but not axially coupled to said drive shaft,
   wherein said plunger element is threaded so that the dose limit nut is engaged with said plunger element via said thread, in order to guide relative axial movement between the dose limit nut and the plunger element,
   wherein said dose limit nut is provided with dose limiting endstop features which are engageable with one or more formations comprising a change in a depth of said thread of the plunger element so as to limit axial travel of said dose limit nut with respect to said plunger element, so as to limit maximum and minimum doses of medicament which can be set by the user, and
   wherein said dose limit nut further comprises a last dose rotary endstop feature which prevents further rotation of said dose limit nut with respect to said drive shaft so as to prevent the user from setting a dose that is greater than an injectable volume of medicament remaining in said medicament container.

2. The injection device of claim 1 wherein one of said dose limiting endstop features also comprises said last dose rotary endstop feature.

3. The injection device of claim 1 wherein said drive shaft is arranged concentrically around a first longitudinal axis and wherein said medicament container and at least part of said drive assembly are arranged around a second longitudinal axis which is substantially parallel to but offset from the first longitudinal axis.

4. The injection device of claim 3 wherein said plunger element comprises a rack and the drive assembly further comprises a worm gear engaged in said rack wherein rotation of said worm gear causes the rack to advance axially forward or backward with respect to said worm gear.

5. The injection device of claim 4 wherein said last dose rotary endstop feature is engageable with said worm gear.

6. The injection device of claim 4 wherein said worm gear is arranged around said first longitudinal axis and said rack is arranged around said second longitudinal axis.

7. The injection device of claim 4 wherein the drive assembly further comprises a worm gear rotational lock engageable with the worm gear.

8. The injection device of claim 7 wherein the worm gear rotational lock is disengageable from a forward end of the worm gear by being pushed axially forward by the drive shaft.

9. The injection device of claim 7 wherein the worm gear rotational lock engageable with the worm gear is engageable in a forward end thereof, so as to substantially prevent rotation of the worm gear.

10. The injection device of claim 4 wherein the drive assembly further comprises means engageable between the drive shaft and the worm gear and which, when engaged, rotationally lock the drive shaft and worm gear together.

11. The injection device of claim 1 wherein the drive assembly comprises a rotational to axial coupling, where the drive assembly is rotationally drivable by a torsion spring and is arranged to provide said axial force for ejecting the dose from the medicament container.

12. The injection device of claim 1 wherein said dose limit nut has a male thread and said plunger element has a female thread.

13. The injection device of claim 1 wherein said dose limit nut has a female thread and said plunger element has a male thread.

14. The injection device of claim 1 wherein said maximum dose is 100 IU.

15. The injection device of claim 1 wherein said minimum dose is 0 IU.

16. The injection device of claim 1 further comprising the medicament container.

17. The injection device of claim 16 further comprising a medicament contained in the medicament container.

18. The injection device of claim 17 wherein the medicament is selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

* * * * *